United States Patent [19]
Igo et al.

[11] Patent Number: 5,725,492
[45] Date of Patent: Mar. 10, 1998

[54] EXTRACORPOREAL CIRCULATION APPARATUS AND METHOD

[75] Inventors: Stephen R. Igo, Clear Lake Shores; James W. Meador, Houston, both of Tex.

[73] Assignee: Cormedics Corp, Clear Lake Shores, Tex.

[21] Appl. No.: 610,622

[22] Filed: Mar. 4, 1996

[51] Int. Cl.$^6$ .................................................. A61M 37/00
[52] U.S. Cl. .................................................. 604/4; 604/23
[58] Field of Search .............................. 604/4–6, 23, 24, 604/26, 29; 422/44, 45, 48

[56] References Cited

PUBLICATIONS

Bernabel A., et al., "*Iloprast and Echistatin protect platelets during simulated extracorporeal circulation,*" ANN. THORAC. SURG. 1995; 59:149–153.

J.H. Gorman and L. Henry Edmunds, Jr., "*Blood Anesthesia for Cardiopulmonary bypass,*" J. CARD. SURG. 1995, 10, 270–279.

Hammon J.W. et al., "Augmentation of Microvascular Nitric Oxide Improves Myocardial Performance Following Global Ischemia," J. CARD. SURG., 1995, 10 (Supp), 423–427.

Sly K., et al., "*Inhibition of Surface–Induced Platelet Activation By Nitric Oxide,*" ASAIO Journal 1995;41:M394–M398.

Yao S., et al., "*Endogenous And Exogenous Nitric Oxide Protect Intracoronary Thrombosis And Reocclusion After Thrombolysis*", CIRCULATION, 92:1005–1010, 1995.

L. Henry Edmonds, "*Breaking the Blood–Biomaterial Barrier,*" presented at the Cardiovascular Science and Technology Conference, Washington, D.C., Dec. 9, 1994.

Blackstone E.H. et al "*the Damaging Effects of Cardiopulmonary Bypass,*" in Wu K.K., roxy E.C. (eds), PROSTAGLANDINS IN CLINICAL MEDICINE:CARDIOVASCULAR AND THROMBOTIC DISORDERS, Chicago, Yearbood Medical Publishers, 1982, pp. 355–369.

Primary Examiner—John G. Weiss
Assistant Examiner—Ki Yong O
Attorney, Agent, or Firm—Tim L. Burgess

[57] ABSTRACT

Patient blood in an extracorporeal flow circuit (such as a cardiopulmonary bypass machine) is contacted with one or more nitric oxide feeds at least one of which is upstream of the circuit pump, to provide a concentration of nitric oxide in the blood effective to inhibit activation of blood platelets and reduce whole body inflammation of the patient as a result of a procedure using the extracorporeal circulation.

13 Claims, 7 Drawing Sheets

1

EXTRACORPOREAL CIRCULATION APPARATUS AND METHOD

FIELD OF THE INVENTION

This invention relates to apparatus and methods for passing a patient's blood from his body to a location outside the body and then returning it to the patient, especially apparatus for treating the blood while outside the body, for example, by dialysis, perfusion, heat exchange or oxygenation, and more particularly, relates to methods and means for reducing whole body inflammation side effects in the patient caused by contact of the blood with surfaces outside the body.

BACKGROUND OF THE INVENTION

Numerous techniques have been developed for circulating the blood of a patient outside the body in an "extracorporeal" circuit and then returning it to the patient during a surgical procedure. For example, in dialysis for patients with kidney failure, blood is circulated extracorporeally and contacted with a large membrane surface separating the blood from a dialysate solution, and urea and other blood chemicals are migrated across the membrane to cleanse the blood, which is then returned to the patient. In ex vivo organ perfusion, such as liver perfusion for patients with liver failure, blood is circulated extracorporeally and perfused through a donor organ, typically a pig liver in the case of liver perfusion, before returning it to the patient. In cases of thermal treatment, blood is circulated out of the body and through a heat exchanger and returned to the body. In heart surgery, either or both ventricles of the heart may be isolated and surgically repaired while making use of the patient's lungs during the surgery. In left monoventricular surgery, the left ventricle is isolated for surgery by cannulating the left atrium into an extracorporeal circuit which pumps the blood into a cannulated femoral artery or other arterial source to the arterial bed. In biventricular surgery, the right ventricle is isolated for surgery by cannulating the right atrium and feeding the blood extracorporeally to the pulmonary artery, and the left ventricle is isolated by cannulating the left atrium and feeding the oxygenated blood extracorporeally to a femoral or other artery for perfusion of the arterial bed.

Another example of extracorporeal circulation is cardiopulmonary bypass ("CPB"), the procedure of mechanically bypassing both the heart and lungs to allow the whole heart to be isolated for surgical repair. A CPB machine, consisting of a number of independent and discrete components linked together by plastic tubing, assumes the function of the heart and lungs by oxygenating the blood of the patient, returning the oxygenated blood to the body, and pumping it through patient's circulatory system. More particularly, in CPB the patient's inferior and superior venae cava are cannulated and the blood is ducted from the patient to a venous reservoir in the CPB circuit. From the venous reservoir, this circuit then connects to a pump which circulates the blood. The blood is then oxygenated by being pumped through a gas exchange reservoir ("oxygenator") where oxygen is added and carbon dioxide is removed from the system. The next CPB element is the heat exchanger where the temperature of the blood can be altered and controlled. This device is typically coupled in parallel to the oxygenator. The last element of the extracorporeal circuit is typically a filter used to eliminate particulate matter accumulated in the extracorporeal system. The oxygenated blood then enters the body of the patient through another cannula in the arterial system. Other elements which are part of the CPB system but operated in parallel to the circuit include systems used to retain suctioned blood in the operative field to return to the patient ("cardioplegia") and systems to filter and concentrate the cells also to be given to the patient through the CPB circuit (cell savers or hemoconcentrators).

Extracorporeal circulation of a patient's blood causes bleeding and thrombotic complications, fluid retention and temporary dysfunction of every organ system. The reason is because contact of the blood with the foreign surfaces of the extravascular circuit triggers a massive defense reaction in blood proteins and cells that has been called "the whole body inflammatory response." The problem has especially been documented in connection with CPB surgery. See Blackstone E. H. et al *"The Damaging Effects of Cardiopulmonary Bypass,"* in Wu K. K., Roxy E. C. (eds), PROSTAGLANDINS IN CLINICAL MEDICINE: CARDIOVASCULAR AND THROMBOTIC DISORDERS, Chicago, Yearbook Medical Publishers, 1982, pp. 355–369, incorporated herein by reference.

In the "whole body inflammatory response" platelets are activated by contact with surfaces other than the endothelial cells that line the circulatory system of the body. The activated platelets adhere to non-endothelial cell surfaces, then aggregate and release granule contents and synthesize powerful vasoconstrictor substances. These granules in turn release coagulation proteins, substances that increase capillary permeability and attract neutrophils, substances that enhance platelet adhesion and aggregation, and numerous other substances including vasoconstrictors norepinephrine, serotonin and histamine, and potent hydrolases and proteases. These granule products contribute to systemic inflammatory response associated with extracorporeal blood circulation. Deficiencies of platelet number and function after extracorporeal circulation such as in CPB are a major cause of postoperative bleeding. Neutophils are strongly activated by extracorporeal circulation and release many cytotoxic chemicals and powerful enzymes that mediate much of the inflammatory response associated with extracorporeal circulation. Interstitial fluid accumulates rapidly especially during CPB caused by increased capillary permeability, increased central venous pressure and decreased colloid osmotic pressure due to hemodilution. Vasoactive substances released by the defense reaction cause endothelial cells or vascular smooth muscle cells to contract or relax or alter the contractile strength of cardiac myocytes. Circulation of these substances contributes to fluid retention and the whole body inflammatory response. Microemboli including fibrin, denatured protein and platelet aggregates too small for capture by extracorporeal circulation filters bombard the organs and may be responsible in CPB procedures for subtle central nervous system deficits that afflict over 50% of patients and can persist for more than a year.

In order to prevent blood from clotting in extracorporeal circulation procedures, heparin is systemically administered to the patient, but heparin does not prevent the whole body inflammatory reaction. This is because heparin acts primarily at the end of the coagulation cascade and does not prevent activation of at least five plasma protein systems (contact; intrinsic coagulation pathway; extrinsic coagulation pathway; complement; and fibrinolysis) and five blood cells (platelets, neutrophils, monocytes, endothelial cells and lymphocytes) which act to produce more than two dozen vasoactive substances that alter the vascular tone, capillary permeability and cardiac myocyte contractability. Heart-lung machines often have heparin coated surfaces, and these seem to be thromboresistent, apparently because they are instantly covered with layers of plasma proteins which isolate the surface from direct contact with flowing blood.

However, all attempts to produce nonthrombogenic synthetic materials have failed. Although some materials are less thrombogenic than others, all activate blood elements to initiate clotting and activate the body's defense reaction. See generally, L. Henry Edmonds, "*Breaking the Blood-Biomaterial Barrier,*" presented at the Cardiovascular Science and Technology Conference, Washington, D.C., Dec. 9, 1994 (reprints available from the author at Dept. of Surgery, 4 Silverstein, Hospital of the University of Pennsylvania, 3400 Spruce Street, Philadelphia, Pa. 19104), and J. H. Gorman and L. Henry Edmunds, Jr., "*Blood Anesthesia for Cardiopulmonary bypass,*" J. CARD. SURG. 1995, 10, 270–279, both incorporated herein by reference.

Although the search for a bioactive material that does not activate blood elements during extracorporeal circulation such as CPB is one approach, another is research into bioactive substances that can temporarily prevent the initial reactions of blood elements that are activated by direct contact with the proteins adsorbed onto biomaterials. An example is the work reported in "*Iloprast and Echistatin protect platelets during simulated extracorporeal circulation,*" Bernabel A., et al., ANN. THORAC. SURG. 1995; 59:149–153.

Only the endothelial cell lining of the blood vessels in the circulatory system is nonthrombogenic. It achieves this property by active metabolic processes and its ability to attract only specific plasma proteins when appropriate. The endothelial cells continuously produce and release local bioregulatory factors into the blood stream and vessel walls. In the normal vessel these endogenous factors regulate platelet adhesion and aggregation in the blood stream (clotting) while in the vessel wall they inhibit neutrophil adhesion and chemotaxis (inflammation), and maintain vascular tone (vasodilation). Nitric oxide (NO), an endothelium derived relaxing factor, plays a key role in regulating platelet activation. See "*Endogenous And Exogenous Nitric Oxide Protect Intracoronary Thrombosis And Reocclusion After Thrombolysis*", Yao S., et al., CIRCULATION, 92:1005–1010, 1995. Endothelial cells synthesize nitric oxide from nitrogen atoms of the amino acid L-arginine through the action of a soluble enzyme [Pharmacological Reviews 43:109, 1991]. This vital biochemical system, called the L-arginine/nitric oxide pathway, also exists in other cells and has been shown to modulate the reactivity of stimulated platelets, neutrophils and smooth muscle cells. In the blood stream, nitric oxide is inactivated by hemoglobin, which explains its short half-life and localized effects. L-arginine and nitric oxide donor substances have been used to supplement blood cardioplegia and reperfusion to preserve endothelial cell function and reverse postcardioplegia contractile dysfunction to hearts exposed to global myocardial ischemia during cardiac surgery. See "*Augmentation of Microvascular Nitric Oxide Improves Myocardial Performance Following Global Ischemia,*" Hammon J. W. et al., J. CARD. SURG., 1995, 10 (Supp), 423–427. Nitric oxide has been under limited investigation as an approach to reduce platelet aggregation by artificial surfaces during CPB. See, "*Inhibition Of Surface-Induced Platelet Activation By Nitric Oxide,*" Sly K., et al., ASAIO Journal 1995;41:M394–M398, in which nitric oxide was added to the oxygenator sweep gas of a membrane oxygenator of a CPB model and some reduction of platelet aggregation was seen, along with decreased rates of platelet aggregation.

SUMMARY OF THE INVENTION

In accordance with our invention, an improvement is provided in extracorporeal circulation apparatus to inhibit activation of platelets coming into contact with the surface of the fluid circuitry of such apparatus, thereby effecting a reduction or prevention of the whole body inflammation response heretofore associated with use of such apparatus.

Our invention includes an extracorporeal blood circulation apparatus comprising an inlet line adapted to receive blood from a patient, an outlet line adapted to return blood to the patient, a fluid circuit for fluid communication between the inlet and the outlet line, at least one pump acting on the fluid circuit to circulate blood therethrough and out the outlet line, and one or more nitric oxide feeds to said fluid circuit, at least one of which is "upstream" of said pump. (Referring to the patient's inflow of blood as the source of an extracorporeal blood stream, "upstream" means closer to that source in the fluid blood circuit.) Such a blood fluid circuit includes the monoventricular and biventricular bypass circuits described above. The fluid circuit may also include a blood treatment portion such as a dialysis component, an organ perfusion component, a heat exchange component or an oxygenation component for blood treatment as discussed above. In this latter instance, at least one nitric oxide feed to the fluid circuit is upstream of at least the blood treatment portion, and preferably is upstream of both the blood treatment portion and the pump. The object is to place a nitric oxide feed as far upstream in the fluid circuit as is practicable for the particular apparatus, in order to minimize the opportunity for platelet contact with foreign surfaces during a transit time while they are not guarded from activation by nitric oxide. Because of the very short half-life of nitric oxide in blood, one or more feeds of nitric oxide are employed, as necessary in the particular circuit, to maintain the concentration of nitric oxide in the circulating extracorporeal blood at a dosage effective to produce the desired inhibition of platelet activation over a period of time sufficient for the journey through the extracorporeal circulation apparatus yet insufficient to sustain the inhibition after the blood is returned to the patient.

This invention also includes means to control administration of nitric oxide to the entering blood at desired dosage rates or concentrations effective to produce the desired inhibition of platelet activation for the journey through the extracorporeal circulation apparatus. A nitric oxide feed comprises a controller for controlling gas pressure and rate of flow into the circuitry, preferably in relation to a volume in or rate of blood flow through the circuitry, optionally delivering the nitric oxide gas to the blood circuitry in a pulsatile manner.

This invention particularly improves the conventional cardiopulmonary bypass machine to allow nitric oxide to be intimately contacted with the blood upon the blood entering the CPB circuit, thereby preventing or greatly reducing the activation of platelets and neutrophils and other blood components normally caused by contact of the blood with the perfusion circuit of the CPB machine. In this invention, at least one contacting location is upstream of the CPB oxygenator in the CPB perfusion circuit and at least one contacting location preferably is as near the entrance to the CPB perfusion circuit as practicable. In contrast to the present invention, if nitric oxide is introduced into or after the oxygenator portion of the perfusion circuit, as described by Sly et al., ASAIO Journal 1995;41:M394–M398, described above, such introduction is too late to inhibit activation of enough blood platelets sufficiently to adequately control reduction of the whole body inflammation response. In addition, because of the high oxygen tension at the oxygenation membrane, control of dosage rates effective to inhibit activation of platelets at low optimal dosage rates that will not sustain platelet activation inhibition upon return of the dosed blood to the patient is enormously complicated, if not lost altogether, by rapid conversion into nitrogen dioxide of the nitric oxide introduced at the oxygenator ($2\ NO + O_2 \rightarrow 2\ NO_2$).

In accordance with our invention, preferably a nitric oxide feed to a CPB machine is a feed to the CPB reservoir or to the fluid circuit immediately downstream to the reservoir, that is, proximate or close to the reservoir and on the side of the reservoir distal to the patient blood source.

Where the feed is to the reservoir, the feed suitably comprises a diffuser for diffusing nitric oxide gas into the reservoir, and comprises a controller for controlling gas pressure and rate of flow into the reservoir, more preferably controlling the pressure and flow in relation to the rate of blood flow from the reservoir. Optionally the controller delivers the nitric oxide gas to the reservoir in a pulsatile action. Suitably the diffuser includes a membrane or filter that is not permeable to blood and is permeable to nitric oxide gas and through which nitric oxide is introduced into the reservoir. The rate of introduction is sufficient to allow nitric oxide diffusion in solution in the blood plasma but preferably not so great as to permit bubble formation in the reservoir. Bubble formation less efficiently limits contact area to the bubble surface area of the liquid-gas interface.

Suitably where a nitric oxide feed to the fluid circuit is immediately downstream from the reservoir, the feed comprises a tubular membrane having an inlet, the membrane being disposed longitudinally within the fluid circuit adapted to contact blood flowing along the exterior thereof and being permeable to nitric oxide gas diffusion into solution in the blood plasma and impermeable to any nitrogen gas carrier introduced into the interior thereof through the inlet. Preferably the feed comprises a controller for controlling gas pressure and rate of flow into the membrane and the controller controls the pressure and flow in relation to the rate of blood flow through the CPB machine so that the concentration of nitric oxide in the blood remains within a desired range regardless of changes in the rate of flow of blood through the CPB machine. The controller may deliver the nitric oxide gas into the membrane in a pulsatile action. The membrane may include an outlet and a gas scavenger may be connected to the membrane outlet for capturing any nitric oxide leaving the membrane.

DESCRIPTION OF THE DRAWINGS

The present invention may be more completely and easily understood when taken in conjunction with the accompanying drawings, in which.

DESCRIPTION OF PREFERRED EMBODIMENTS

Figure 1:
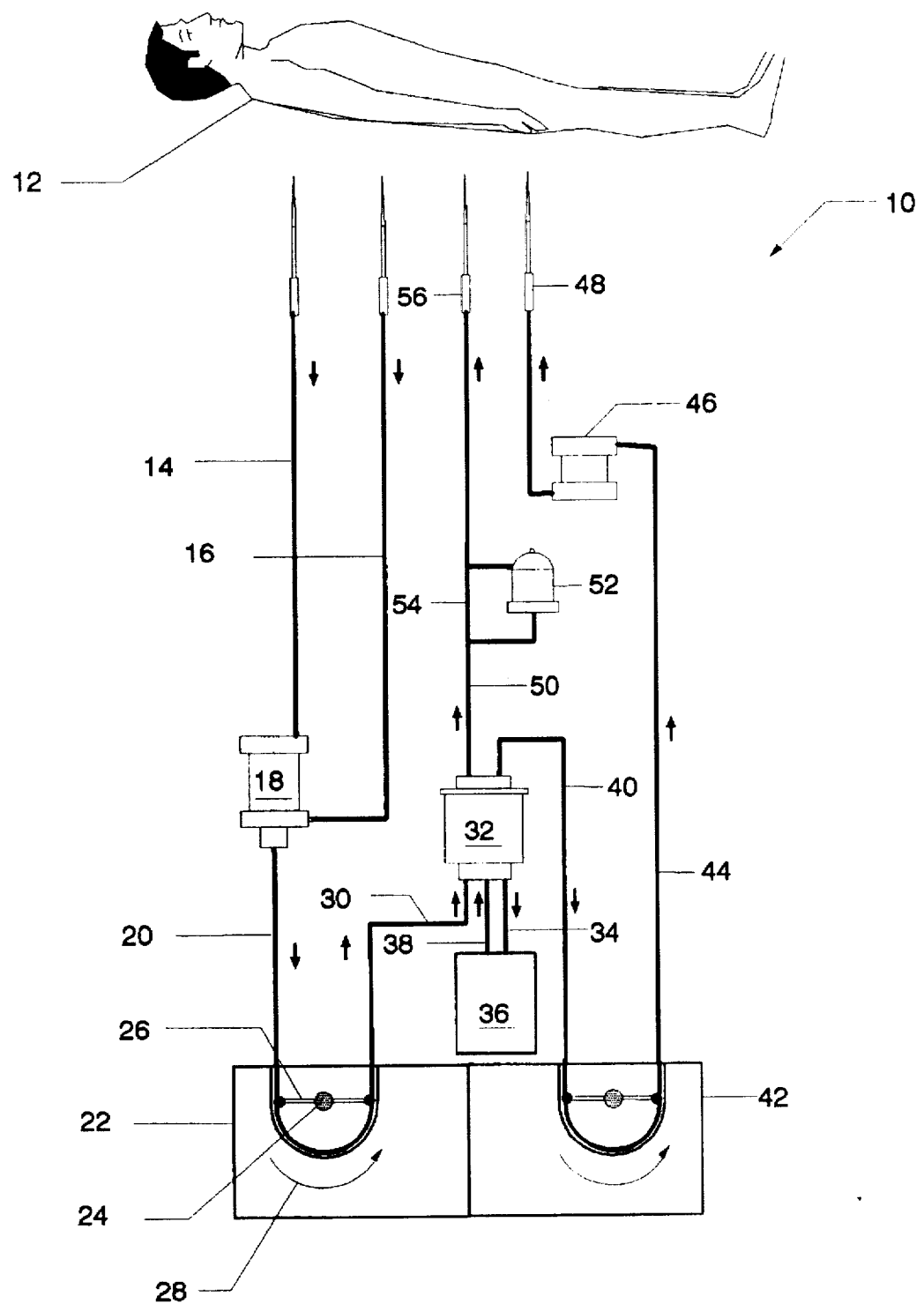
FIG. 1 is a schematic illustration of a prior art cardiopulmonary bypass circuit.

Referring to FIG. 1, a typical CPB circuit is indicated generally by reference numeral 10. The patient is shown by numeral 12. A venous cannula 13 inserted into the patient is connected into a fluid inlet tube 14 that directs blood from the patient to a venous reservoir 18. Another cannula 15 inserted in the patient is connected to another fluid inlet 16 that also leads from the patient to venous reservoir 18. Reservoir 18 may be a pole mounted unit or may be located on the heart-lung machine table, but in either case normally is the first fixed point in the circuit, lines 14 and 16 normally being flexible and long enough to allow surgeon and surgical assistants room to maneuver around the surgical table. The purpose of venous reservoir 18 is to accumulate the admitted blood for feeding the balance of the CPB circuit. The accumulator eliminates pump starvation and cessation of pump prime by providing a buffer from ebb and flow of blood from the patient.

From the venous reservoir, plastic tubing 20 leads to the inlet side of a roller pump 22. Roller pump 22 has a hub 24 from which protrude two arms 26. These arms impinge on the tubing 20 collapsing it. Rotation of the pump hub 24 in the direction indicated by reference numeral 28 provides the desired flow direction and flow rate. The blood leaves the roller pump 22 through tubing 30 to the inlet of the oxygenator 32. The blood can be thermally adjusted by passing it from the oxygenator 32 through tubing 34 into a heat exchanger 36 for heating or cooling before returning to the oxygenator 32 by tubing 38. Upon oxygenation, the blood exits the oxygenator in two ways. The first way is through tubing 40 to another roller pump 42, from there pumped through tubing 44 to a cardioplegia system 46, then to the patient 12 through outlet tubing 47 and a cannula 48. The other mechanism with which the blood leaves the oxygenator 32 is through tubing 50. A filter 52 is located on a side branch of this portion of the circuit. When it is desired to use the filter 52, tubing 50 is clamped in the area noted by numeral 54 and the blood travels through the filter 52 before returning to the patient through outlet tubing 57 and a cannula 56. The venous return reservoir 18 is the juncture of all blood removed from the patient. It is at this location where the improvement according to this invention suitably may be added to the CPB circuit, prior to the pump 22 and the blood treatment oxygenator 32.

Figure 2:
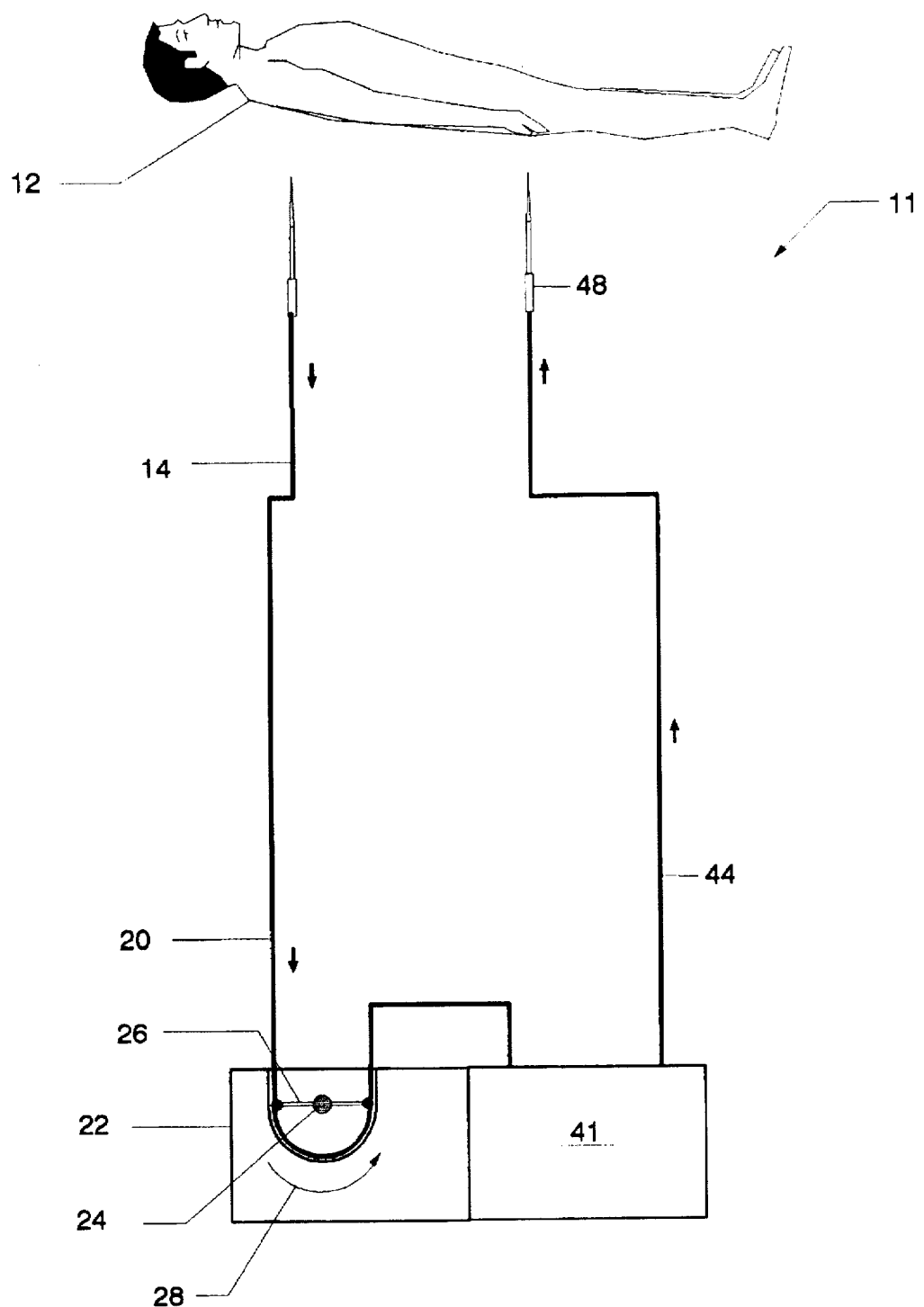
FIG. 2 is a schematic illustration of a prior art blood treatment circuit in general.

FIG. 2 depicts an extracorporeal blood treatment circuit in general, designated by reference numeral 11, and in which reference numerals are the same for the like elements found in the specific CPB circuit shown in FIG. 1. Reference numeral 41 represents a blood treatment component. In the case of a CPB apparatus as in FIG. 1, blood treatment component 41 comprises at least oxygenator 32 and optionally also heat exchanger 36 with connecting tubing 34, 38 and either or both of (1) the cardioplegia system 46 with associated second pump 42 and connecting tubing 40, 44, 47 and (2) the filter 52 with associated tubing 50. Numeral 17 indicates a blood fluid inlet generally and numeral 49 indicates a fluid outlet for blood return generally to the patient in FIG. 2. In accordance with this invention, blood treatment component 41 of the fluid circuit of the apparatus 11, instead of being an oxygenation system as in FIG. 1, suitably may be a heat exchange system 36, a renal dialysis component for exchange of urea and other blood chemicals with a dialysate solution across an exchange membrane, or an organ perfusion component such as an ex vivo liver and perfusion support system tying into circuit interconnects 30 and 49.

Figure 3:
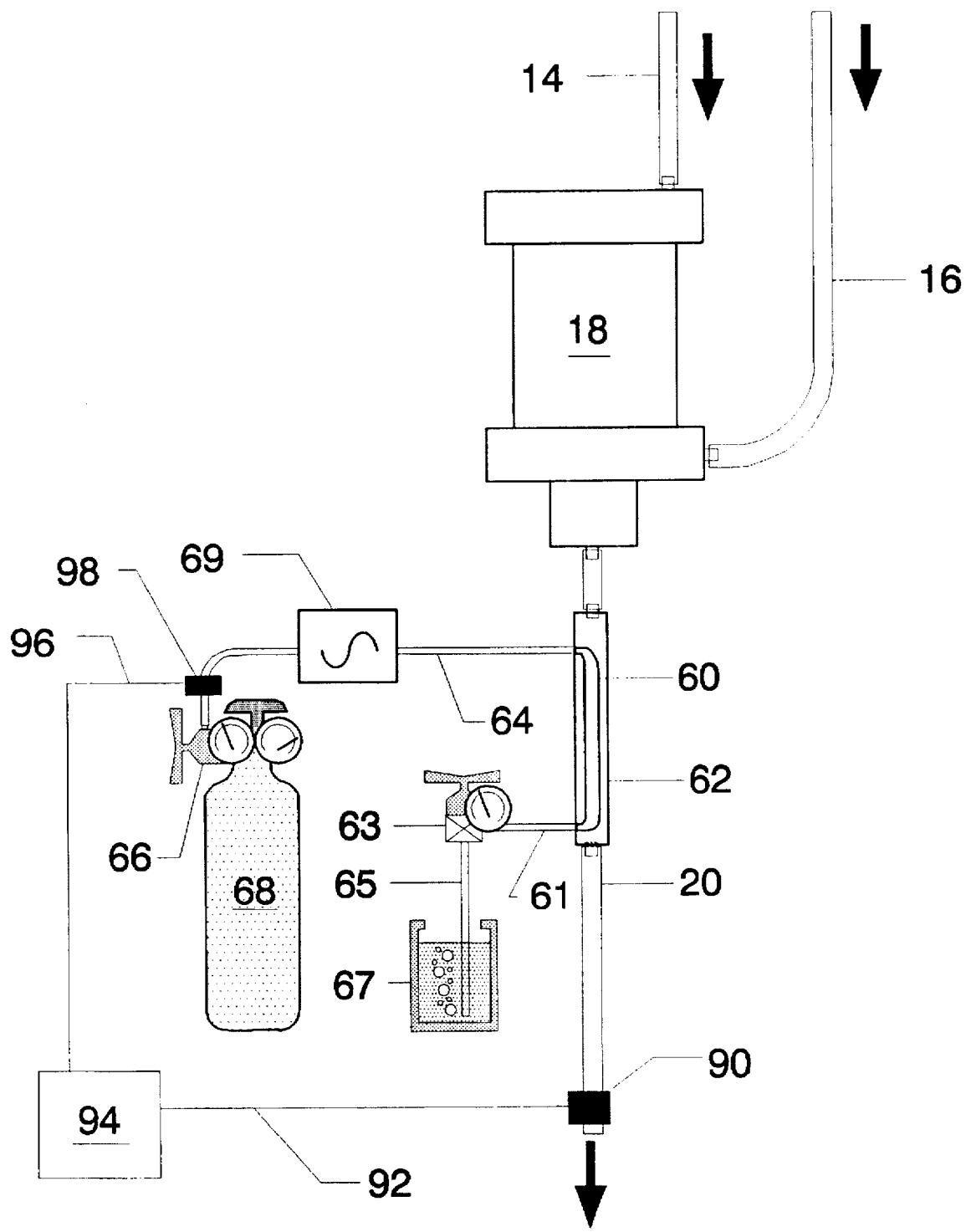
FIG. 3 is a schematic illustration of the initial portion of the cardiopulmonary bypass circuit depicting one embodiment of the invention.

In accordance with this invention, one of more feeds of nitric oxide are employed, as necessary in the particular circuit, to maintain the concentration of nitric oxide in the circulating extracorporeal blood at a dosage effective to produce the desired inhibition of platelet activation over a period of time sufficient for the journey through the extracorporeal circulation apparatus yet insufficient to sustain the inhibition after the blood is returned to the patient and desired dosages. FIG. 3 depicts one such feed at the initial (venous inlet) portion of the circuit illustrated in FIG. 1. In this preferred embodiment of the invention, a gas permeable membrane 60 is located within a conduit 62 of the blood circuit located immediately downstream from the reservoir 18. The gas permeable membrane 60 is elongated and tubular in form and is disposed longitudinally within conduit 62 adapted to come into contact with blood flowing through conduit 62. A gaseous source, a mixture of nitric oxide and a carrier gas such as nitrogen, is housed in container 68 under high pressure. Regulator 66 controls the output gas pressure to periodic driver 69. The purpose of the periodic driver 69 is to induce a sinusoidal shaped pressure curve to the gas much like a "pulse". The gas leaves the driver through tubing 64 and flows into the interior of gas permeable membrane 60. Due to the permeability of this membrane 60 to nitric oxide gas, the gas will diffuse through the membrane and dissolve in the blood plasma where it will come into contact with platelets. The membrane is selected to be impermeable to nitrogen and the nitrogen carrier gas will not diffuse through the membrane. Coupled to the outlet of the membrane 60 is outlet tubing 61, which is connected to valve 63. Valve 63 adjusts the back pressure of the system. From the valve 63 the carrier gas and any residual nitric oxide gas is carried through tube 65 into container 67, which is filled with a scavenger liquid such as methylene blue. The gas mixture is allowed to bubble up through the container containing the scavenger liquid. The scavenger liquid absorbs any residual nitric oxide so that the only gas that escapes into the atmosphere is the carrier gas.

Blood guarded by dissolved nitric oxide exits conduit 62 and into tubing 20 where is passes by a conventional blood flow measuring device 90. Signals from blood flow measuring device 90 are transferred by line 92 to controller feedback logic component 94 which outputs a signal through line 96 to controller driver component 98 for controlling pressure and flow from regulator 66. The controller system comprising units 90, 94 and 98 with connecting lines 92 and 96 controls the flow of gas into membrane 60 in relation to the flow of blood through tubing 20. In this manner, when the flow rate of the blood is low, the nitric oxide introduction is correspondingly and automatically reduced. Conversely, in cases of high flow the nitric oxide introduction is correspondingly and automatically raised.

The gas permeable membrane 62 has a gas permeable rate K which is dependent on the material of construction and the molecular characteristics of the gas. For nitric oxide, the gaseous release rate from membrane 60 is proportional to K, the exposed surface of the membrane to the blood, the internal gaseous pressure within the membrane and the hydraulic pressure of and gas tension of nitric oxide (if any) in the blood flowing by it. Delivered molecular concentrations to the blood is calculated knowing the above plus the absorption coefficient of the blood to the nitric oxide. Thus the controller controls the gas flow and at a level which, for the characteristics of membrane 60 and the absorption coefficient of nitric oxide gas at the temperature of the blood in the apparatus (before thermal adjustment, if any), is sufficient to provide an actual concentration of nitric oxide in solution effective in the presence of venous red blood cell blood hemoglobin to inhibit platelet activation.

Figure 4:
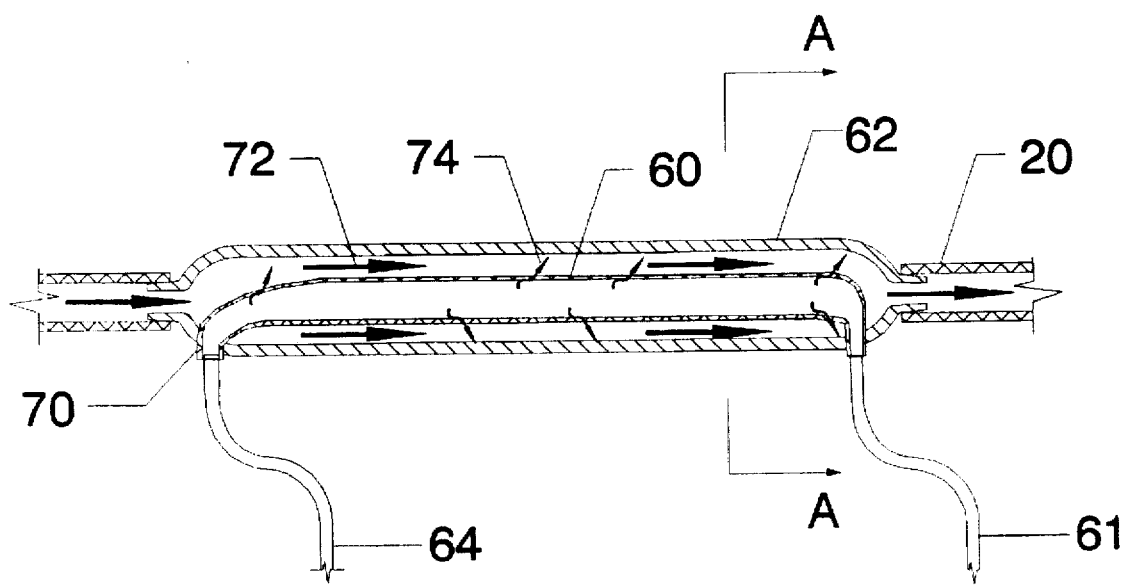
FIG. 4 is a side view of a longitudinal section of flow components of the embodiment of the invention depicted in FIG. 3.

FIG. 4 illustrates a longitudinal sectional view of the conduit 62, the gas permeable membrane 60 and the tubing 64. Nitric oxide gas flows into the membrane 60 at location 70. As the gas pressure inside the gas permeable membrane 60 exceeds the pressure of the blood within conduit 62, nitric oxide gas will diffuse from the membrane into the blood stream as indicated by arrows 74. The nitric oxide will be absorbed by the blood cellular components which will mediate the inflammatory response as described earlier.

Figure 5:
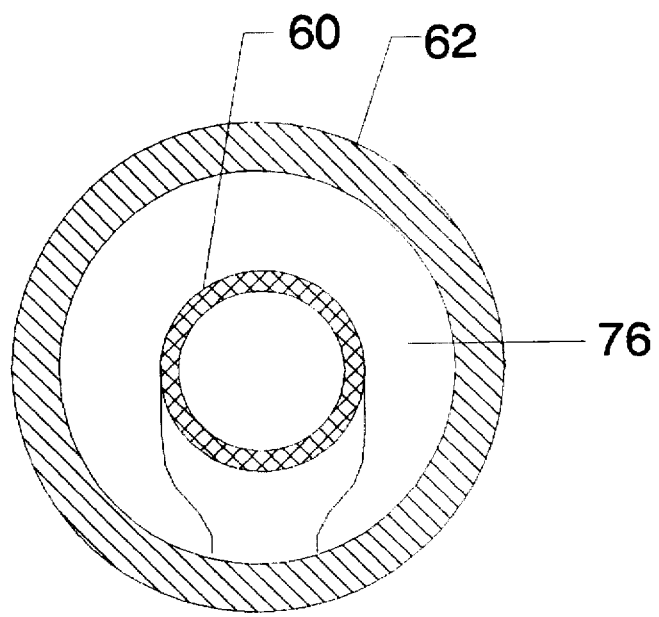
FIG. 5 is an cross section view of the flow of components shown in FIG. 4.

Referring to FIG. 5, which illustrates a cross section of FIG. 3 along the line A—A, the relationship between the geometry's of the conduit 62 and gas permeable membrane 60 is as follows. The cross sectional area of the inside of conduit 62 minus the sectional area of the gas permeable membrane 60 (such difference being referenced by numeral 76) is approximately equivalent to the cross section of the tubing elsewhere in the CPB circuit, (i.e. the cross section of tubing element 20). With this relationship the blood is not subjected to an adverse pressure gradient in conduit 62. Longitudinally, the shape of the gas permeable membrane 60 follows that of the conduit 62, again so that adverse pressure gradients are not imparted into the circuit.

Figure 6:
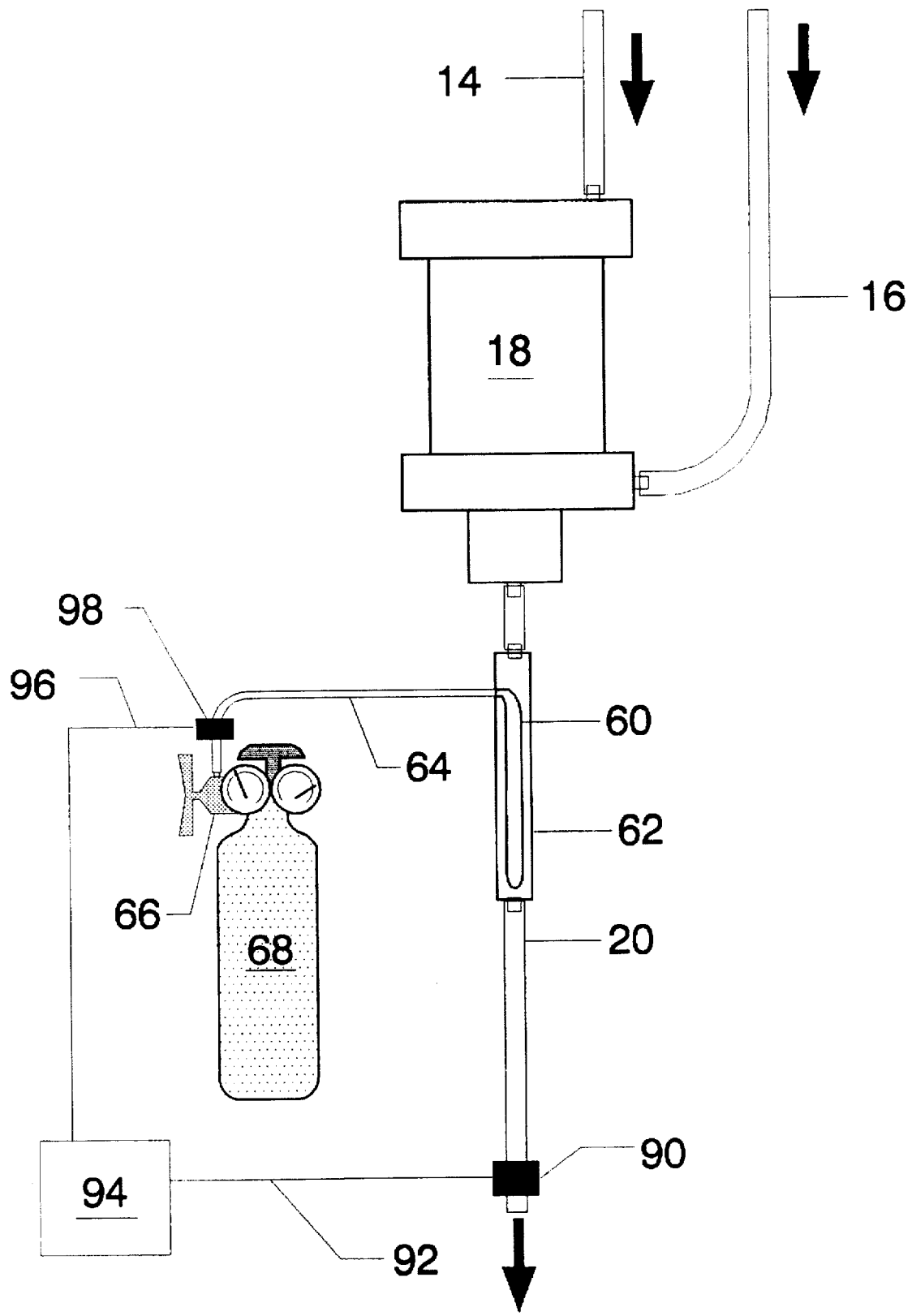
FIG. 6 is an illustration of the initial portion of the cardiopulmonary bypass circuit with the inclusion of another embodiment of the invention.
Figure 7:
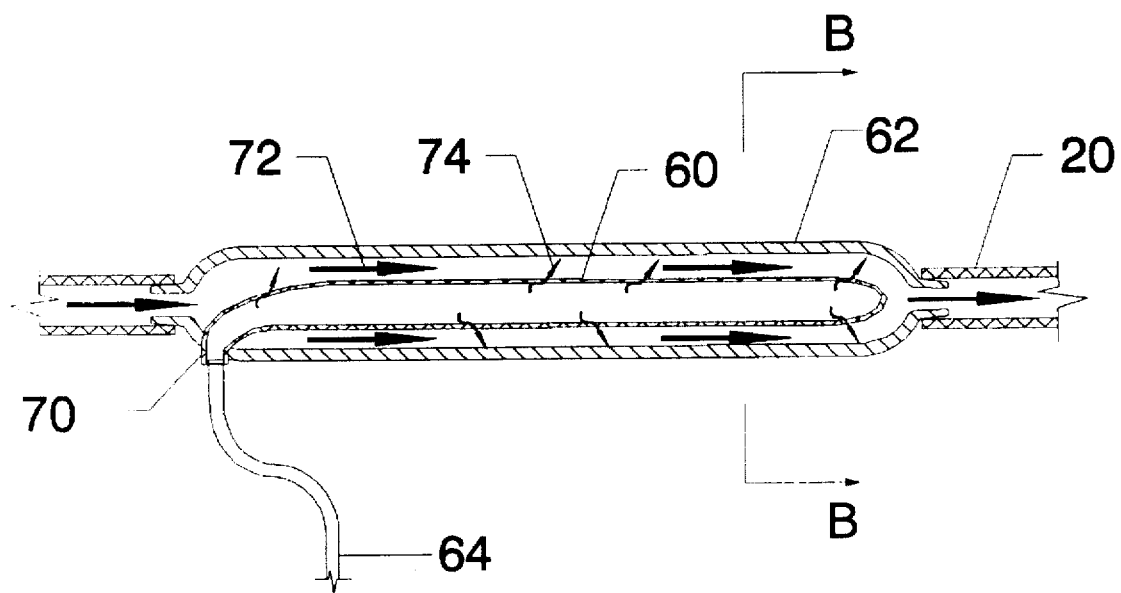
FIG. 7 is a side view of a longitudinal section of flow components of the embodiment of the invention depicted in FIG. 6.
Figure 8:
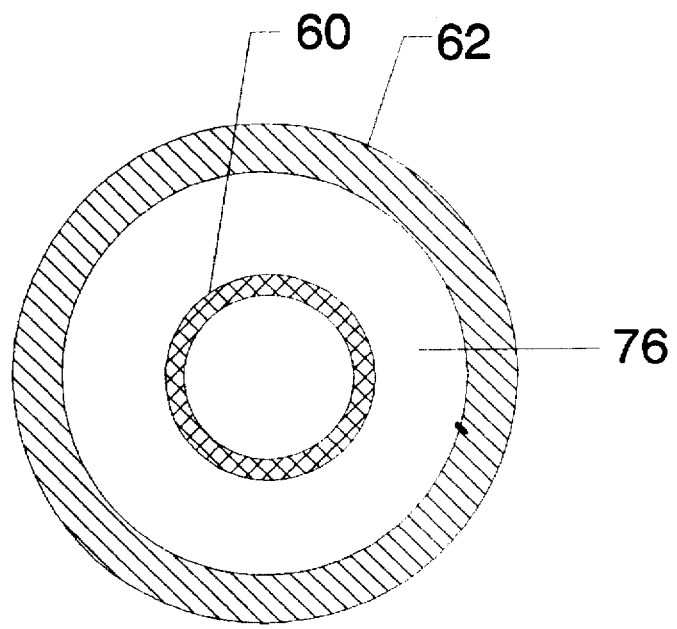
FIG. 8 is a cross section view of the flow of components shown in FIG. 6.

FIG. 6 illustrates another preferred embodiment of the invention. In this embodiment a carrier gas is not used so that container 68 holds a 100% concentration of nitric oxide. A pulse drive generator 69 is not shown but may be present. In this embodiment, there is no outlet conduit of membrane 60. As pressure builds up in conduit 60, the nitric oxide diffuses into the bloodstream as previously described. Because there are no residual carrier gas molecules, there is no need for a return. Simply stated, components 61, 63, 65, and 67 of the embodiment depicted in FIG. 2 are absent at the distal end of membrane 60 and the tube 62 in this configuration. As in the embodiment depicted in FIG. 3, a controller comprising components 90, 94 and 98 with connections 92 and 96 controls the concentration of nitric oxide in solution in the blood. FIG. 8 illustrates a cross sectional view B—B of FIG. 7 with the same numbers used in the same way as in FIG. 5.

The above embodiments illustrate an optimal configuration of the invention in which the blood flows around the external portion of a gas permeable membrane 60. While it is within the scope of this invention that the system can be configured so that the gas is on the external portion of the membrane and blood is flowed within the membrane, in low gas pressure conditions some membranes dilate, increasing the cross sectional area of the membrane and lowering blood flow through that portion of the apparatus, and in high gas pressure conditions, some membranes might collapse, reducing blood flow. In the preferred embodiments, if gas flow is zero, the membrane might collapse but it would not occlude or preclude blood flow.

Figure 9:
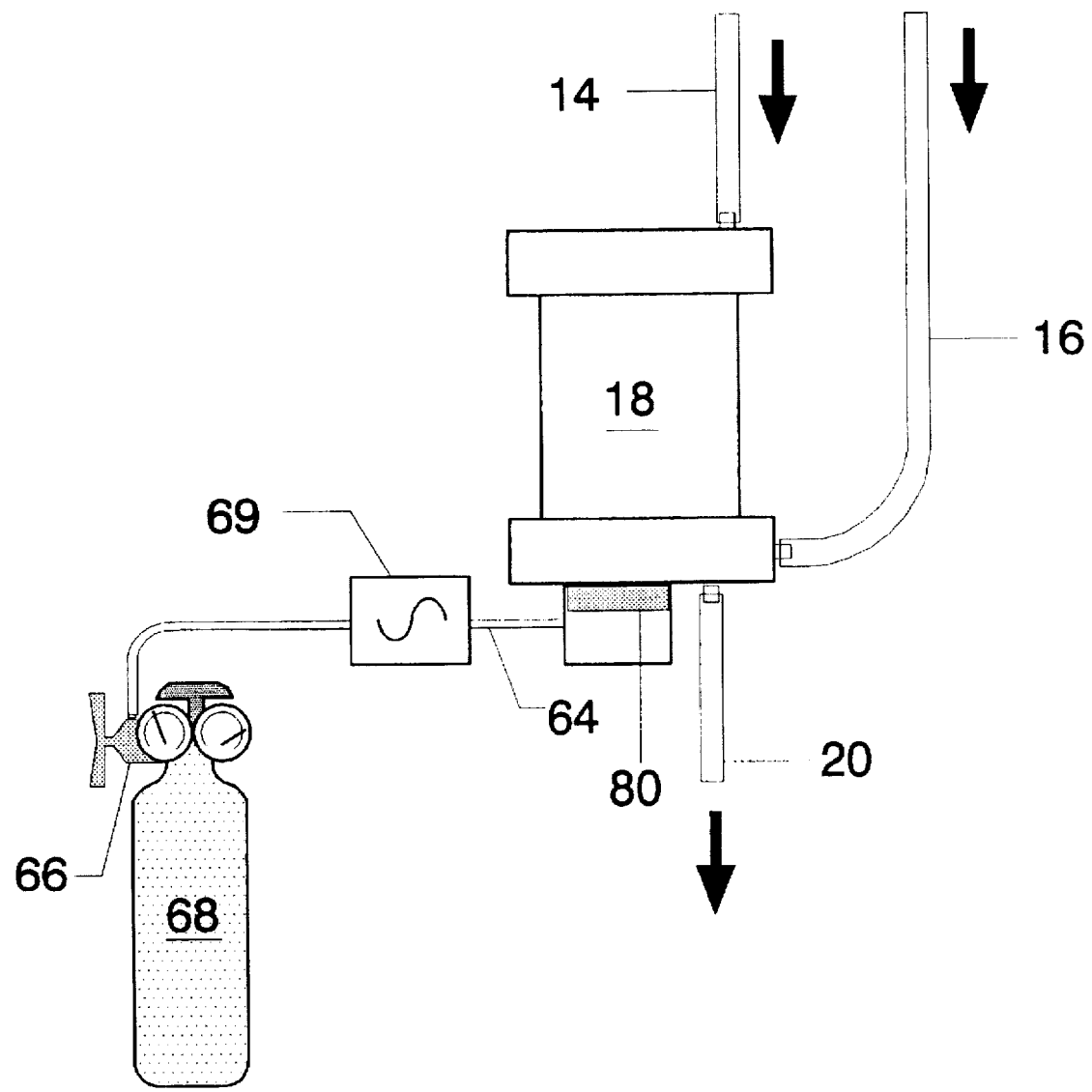
FIG. 9 is a schematic illustration of the initial portion of the cardiopulmonary bypass circuit depicting another embodiment of the invention.

FIG. 9 depicts another embodiment of the invention. In this embodiment the nitric oxide feed is to reservoir 18. The feed comprises a diffuser 100 for diffusing nitric oxide gas into the reservoir, and comprises a regulator 66 for controlling gas pressure and rate of flow into the reservoir and a driver 69 for delivering the nitric oxide gas into reservoir 18 through inlet 64 in a pulsatile manner. Suitably diffuser 100 comprises a membrane or filter 80 that is not permeable to blood and is permeable to nitric oxide gas through which nitric oxide gas is introduced into the reservoir. As in the embodiment depicted in FIGS. 3 and 6, a controller comprising components 90, 94 and 98 with connections 92 and 96 controls the concentration of nitric oxide in solution in the blood.

It is important that the location of the nitric oxide feed be close to the patient cannulation point as possible in the extracorporeal circuit to reduce so much as practicable the period of exposure of platelets to non-endothelial surfaces. At least one feed location is described generally as upstream of the pump that is needed to circulate the blood extracorporeally through the system and back to the patient. With reference to the FIG. 2, that point is anywhere in line 15. In FIGS. 3–9, which involve a CPB circuit where blood from two inlets 14 and 16 is pooled in reservoir 18, either the reservoir or the tubing immediately past the reservoir is selected for initial introduction of the nitric oxide, for the practical reason that these are the closest stationary locations in the system to the patient source of blood and also because control of nitric oxide introduction is most readily accomplished in the reservoir or in the blood filled lines in the immediately downstream tubing under the influence of a pump as opposed to in the blood inlet lines where lines are mobile to allow access to the surgical field, and especially in the case of blood suctioned from the operative field where intermittent blood and air flow occurs. The closest stationary location will vary according to the blood treatment component 41 involved in the use of this invention. Because of the very short half life of nitric oxide in the blood, additional feeds may be used further downstream to maintain the desired nitric oxide concentration in the blood without overdosing the blood in but one location.

The foregoing embodiments in FIGS. 3–9 therefore only illustrate examples of the invention as applied to CPB, and are not to be taken as limiting the scope of the invention, which is defined in the appended claims.

We claim:

1. An extracorporeal blood circulation apparatus comprising circuitry including:
   (a) an inlet line adapted to receive blood from a patient,
   (b) an outlet line adapted to return blood to the patient,
   (c) a fluid circuit for fluid communication between the inlet and the outlet line,
   (d) at least one pump acting on the fluid circuit to circulate blood therethrough and out the outlet line, and
   (e) one or more nitric oxide gas feeds to said fluid circuit, at least one being upstream of said pump,
   (f) a container comprising a source of nitric oxide connected to one or more nitric oxide gas feeds.

2. An extracorporeal blood circulation apparatus comprising circuitry including:
   (a) an inlet line adapted to receive blood from a patient,
   (b) an outlet line adapted to return blood to the patient,
   (c) a fluid circuit for fluid communication between the inlet and the outlet line said fluid circuit including a blood treatment portion,
   (d) one or more nitric oxide gas feeds to said fluid circuit, at least one being upstream of at least said blood treatment portion, and,
   (e) one or more nitric oxide gas feeds to said fluid circuit, at least one being upstream of at least said blood treatment portion, and
   (f) a container comprising a source of nitric oxide connected to one or more nitric oxide gas feeds.

3. The apparatus of claim 2 in which said blood treatment portion comprises a component selected from a dialysis component, an organ perfusion component, a heat exchanger component, an oxygenation component, or a combination of such components.

4. The apparatus of claim 2 in which said feed comprises a controller for controlling gas pressure and rate of flow into the circuitry.

5. The apparatus of claim 4 in which said controller controls the pressure and flow in relation to the rate of blood flow through the circuitry.

6. The apparatus of claim 4 in which said controller delivers the nitric oxide gas to said circuitry in a pulsatile manner.

7. In a cardiopulmonary bypass apparatus comprising circuitry including an inlet line adapted to receive blood from a patient and an outlet line adapted to return blood to the patient, a reservoir connected to the inlet line for accumulation of blood received from the patient, an oxygenator, a fluid interconnection circuit for fluid communication between the reservoir and the oxygenator and between the oxygenator and the outlet line, and at least one pump acting on the fluid circuit to withdraw blood from the reservoir and circulate it through the oxygenator and out the outlet line, the improvement which comprises one or more nitric oxide gas feeds to the circuitry, at least one being upstream of the oxygenator, and a container comprising a source of nitric oxide connected to one or more nitric oxide gas feeds.

8. The apparatus of claim 7 comprising a nitric oxide gas feed to the reservoir.

9. The apparatus of claim 8 wherein said feed comprises a diffuser for diffusing nitric oxide gas into the reservoir.

10. The apparatus of claim 8 in which said diffuser comprises a filter permeable to nitric oxide gas and impermeable to blood and through which nitric oxide gas is introduced into the reservoir.

11. The apparatus of claim 7 comprising a nitric oxide feed to the fluid circuit immediately downstream from the reservoir.

12. The apparatus of claim 11 in which said feed comprises a tubular membrane having an inlet, said membrane being disposed longitudinally within the fluid circuit adapted to contact blood flowing along the exterior thereof and being permeable to nitric oxide gas and impermeable to any nitrogen gas carrier introduced into the interior thereof through said inlet.

13. The apparatus of claim 12 further comprising an outlet from the membrane and a gas scavenger connected to said membrane outlet for capturing any nitric oxide leaving the membrane.

* * * * *